United States Patent [19]

Akopov et al.

[11] Patent Number: 4,684,051
[45] Date of Patent: Aug. 4, 1987

[54] SURGICAL INSTRUMENT

[76] Inventors: Ernest M. Akopov, ulitsa Borisa Galushkina, 12, korpus 2, kv. 28; Valery E. Schitinin, ulitsa Butyrskaya, 53/63, kv. 104; Anna V. Arapova, Krasnostudenchesky proezd, 21, kv. 44, all of Moscow, U.S.S.R.

[21] Appl. No.: 772,733

[22] Filed: Sep. 5, 1985

[51] Int. Cl.[4] .............................................. A61B 17/00
[52] U.S. Cl. ................................ 227/19; 227/DIG. 1; 227/135
[58] Field of Search .................... 227/DIG. 1, 19, 135; 128/334 R

[56] References Cited

U.S. PATENT DOCUMENTS 3,494,533  2/1970  Green et al. .
3,949,923  4/1976  Akopov et al. ............... 227/DIG. 7
4,305,539 12/1981  Korolkov et al. ............ 227/DIG. 7
4,378,901  4/1983  Akopov et al. .

Primary Examiner—Paul A. Bell
Attorney, Agent, or Firm—Fleit, Jacobson, Cohn & Price

[57] ABSTRACT

A surgical instrument for placing linear staple sutures includes a body having a closed rectangular frame. Each of the lateral sides of the frame are provided with a slot which is located on an inner surface of the lateral side close to the adjacent side of the frame. The axis of the slot is parallel to each of the lateral sides. A die is provided with a plurality of recesses and secured on the adjacent side of the frame. The extreme recesses of the die are arranged inside the slots on the frame lateral sides. A staple head is accommodated in the body. A detachable staple magazine has a plurality of staple slots and positioned so that its portions provided with extreme staple slots should engage the slots in the lateral sides of the frame, a staple ejector, and actuators of the staple head and of the staple ejector, respectively.

11 Claims, 22 Drawing Figures

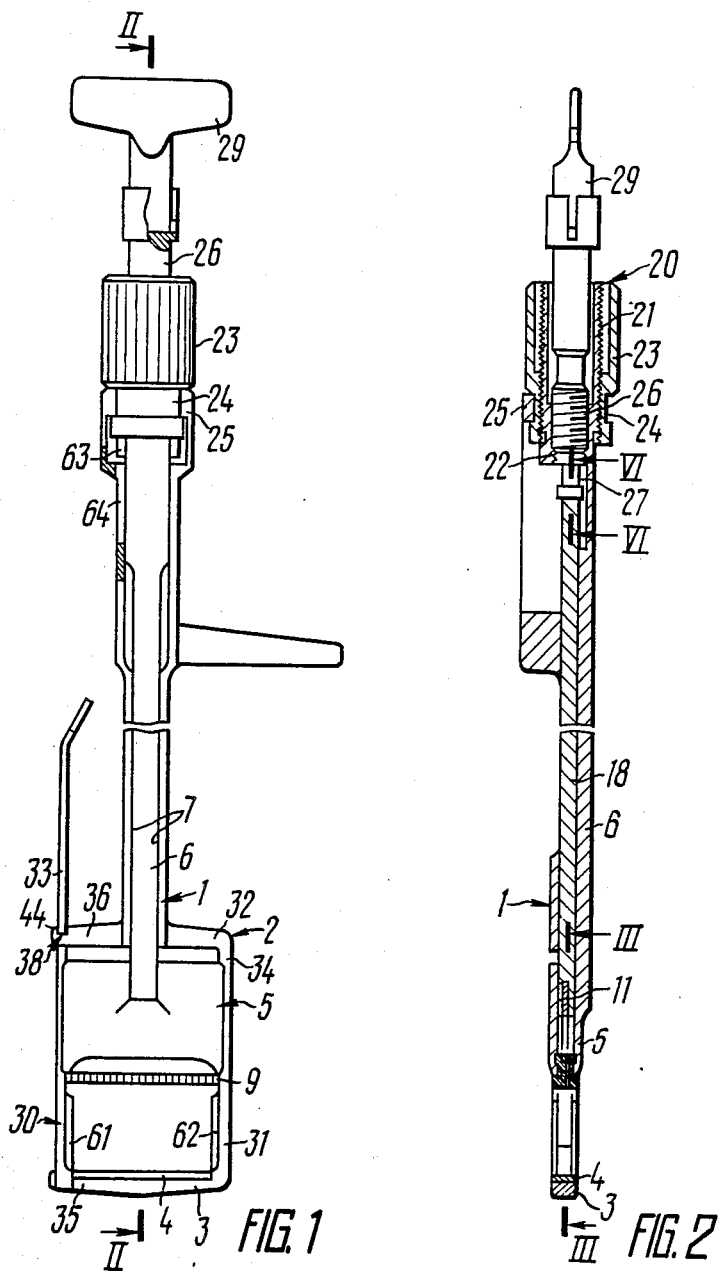

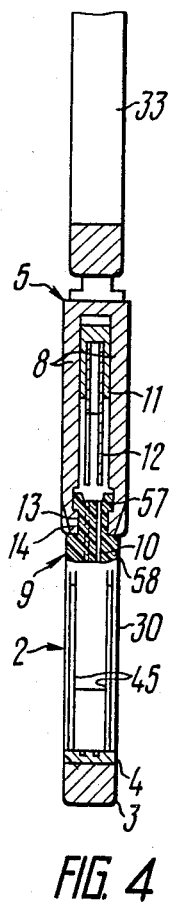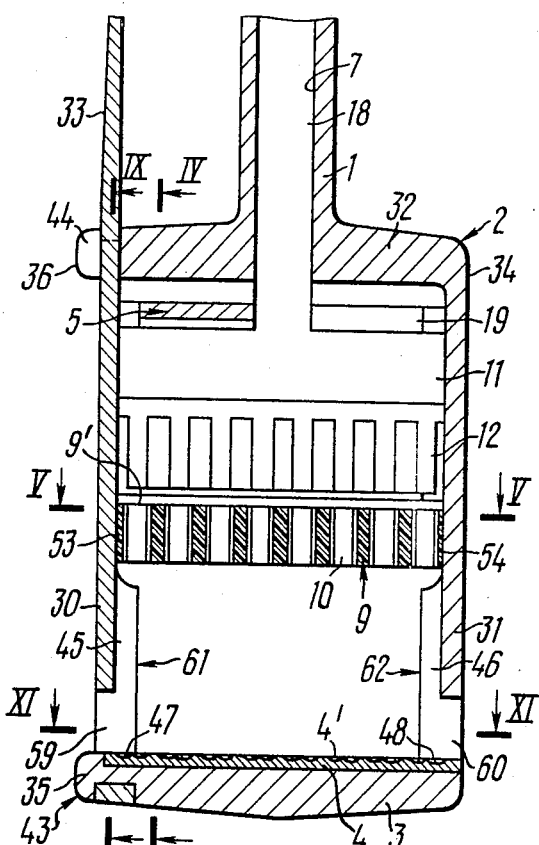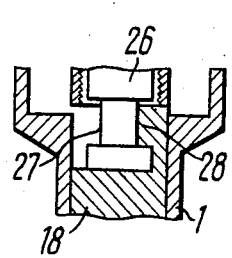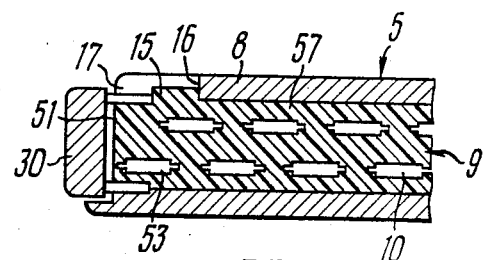
FIG. 4
FIG. 3
FIG. 6
FIG. 5

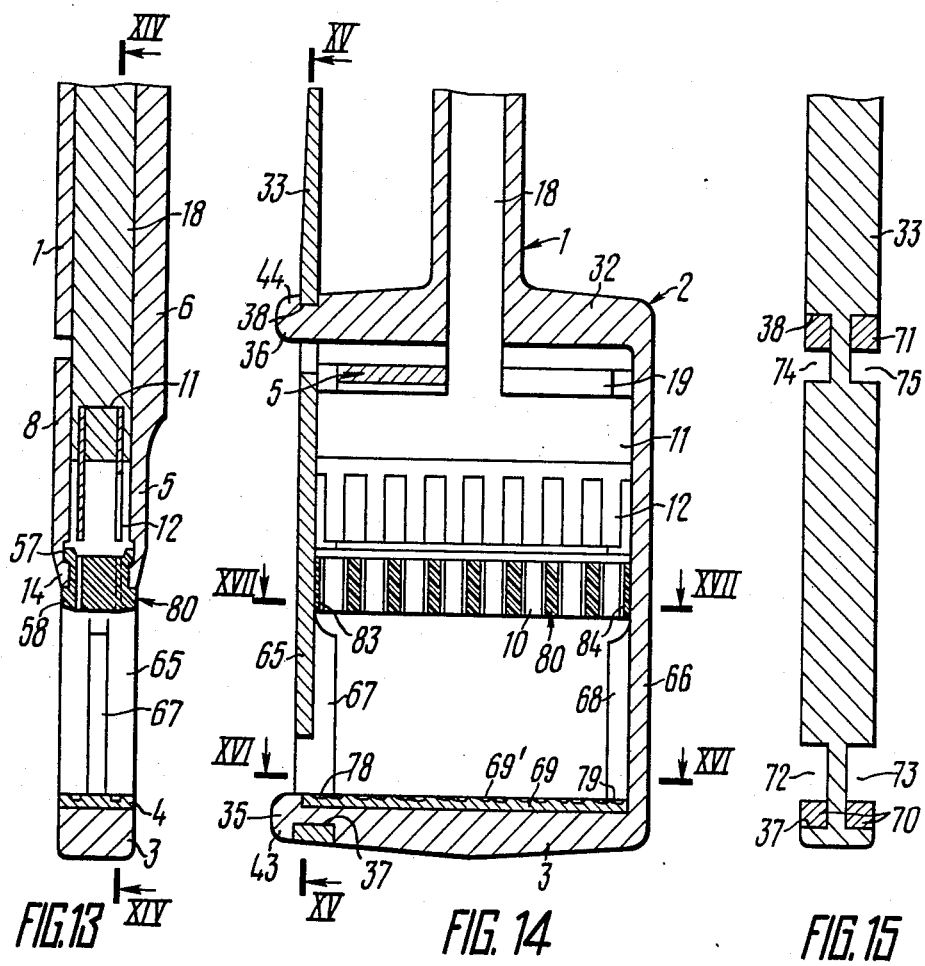

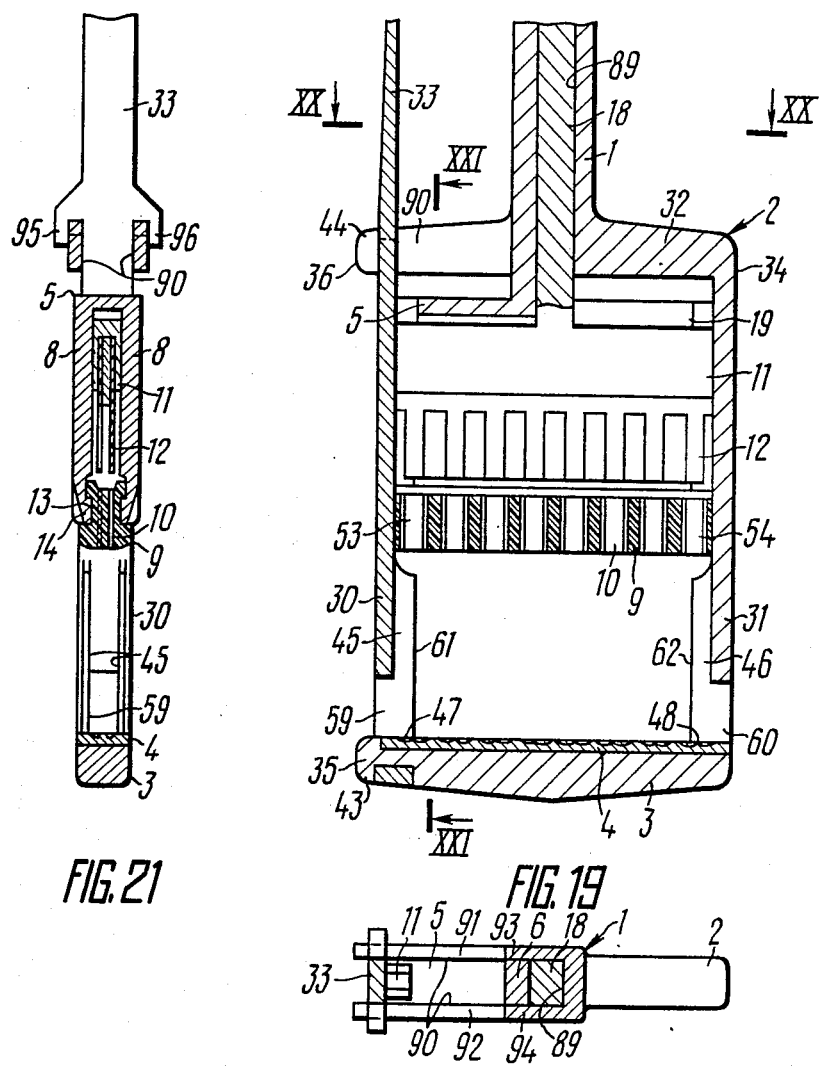

SURGICAL INSTRUMENT

FIELD OF THE INVENTION

The present invention relates to medical equipment and has particular reference to surgical instruments.

The invention can find application for placing linear staple sutures when stitching up various organs, in particular, for stitching up the intestines in surgery of new-born infants and babies, for surgery in hard-of-access places, e.g., for stitching up the organs lying deeply in the small pelvis, and also for suturing blood vessels in vascular surgery.

BACKGROUND OF THE INVENTION

Known in the present state of the art are surgical suturing instruments (otherwise called stapling machines) for placing linear sutures, comprising a body having a hook which carries a die with a number of recesses, a staple head with a staple magazine and a staple ejector, a tissue restrictor and actuators of the staple head and the ejector [(cf., e.g., U.S. Pat. No. 3,494,533 Int. Cl. B 31b 1/00 issued in 1970 to David T. Green et al.)].

The free end of the hook to which the die is held, is arranged in a cantilevered manner; hence the construction of the stitching portion of the instrument is inadequately rigid in three mutually square directions, i.e., in the direction of suturing and in a plane square thereto. Since the stitching mechanism of the instrument sustains heavy loads during the suturing process, resulting from compression of the walls of organs being sutured and once-through deformation (bending) of a great number of staples, a quality suture cannot be obtained unless a stable mutual arrangement of the die recesses and the magazine staple slots is provided. The required rigidity of the construction to meet this important prerequisite is attained in said instruments due to considerably enlarged cross-sectional dimensions of the elements of the hook, the body frame, and some other components of the stitching mechanism. Comparatively large dimensions of the stitching portion affect adversely the maneuvrability of the instrument and render it inapplicable in narrow body cavities.

Moreover, a relatively large width of the die and staple magazine requires respectively more space for the instrument to set in the suturing position and leads to a comparatively great distance from the staple suture to the line of cut on the tissues carried out along the magazine and die edge and hence to a rude suture obtained. And conversely, when the cross-sectional size of the hook and other components of the stitching mechanism is reduced, this might result in considerable deformation of the mechanism components during the suturing process, an inadmissible increase in the suturing gap, or distortion of the true shape of stitches applied.

The aforementioned disadvantages are eliminated in surgical instruments for placing linear sutures, incorporating a body having a closed frame.

One more prior-art surgical instrument for placing linear sutures is known to comprise a body with a closed rectangular frame, a die provided with a plurality of recesses and secured on one side of the frame, and a staple head set in the frame opposite to the die and mounted movably with respect thereto. A detachable staple magazine is fixed stationary in the staple head, as well as a staple ejector is set therein, which is so arranged as to correspond to the magazine staple slots. The staple head has an actuator accommodated in the instrument body, and the staple ejector actuator is located in the staple head body [cf., e.g., U.S. Pat. No. 4,378,901 Int. Cl. B 25C 5/00 issued in 1983 to Ernest M. Akopov and July G. Shaposhnikov)].

High-rigidity construction of the body with a closed rectangular frame makes it possible, with the load upon the stitching mechanism remaining unaffected in the course of multistaple suture application, to considerably reduce deformation of the instrument components and provide for a stable mutual arrangement of the magazine staple slots and the die recesses, a feature that draws distinction between the instrument under discussion and its analogues. The instrument is able to ensure higher-quality formation of suture stitches and attain better tightness of the suture and hence its better hermeticity and hemostatic character. Higher rigidity of the construction makes it possible to reduce the cross-sectional dimensions of the instrument stitching mechanism and thereby to render it more maneuvrable in the operative wound, to decrease the distance from the suture to the line of cut of the tissues involved and to obtain a more delicate suture.

However, the extreme staple slots of the magazine and the respective extreme die recesses are spaced somewhat apart from the frame lateral side. Besides, since the instruments of the character considered herein are designed for placing double-row sutures with one of the rows offset relative to the other (the so-called staggered-stitch sutures), the distance between the extreme paired magazine slots and die recesses of one row and the respective slots and recesses of other row is as a rule adopted to be half the pitch of stitches in each row. Hence the suture placed on a considerable extension from the frame lateral side is in fact a single-row one.

The aforementioned construction particulars of the instrument under discussion result in that when the instrument is used for suturing an organ whose semiperimeter at the place of suture application equals the distance between the frame lateral sides, the marginal portions of the organ fail to be stitched with staples, or are stitched with a single-row suture over some length. Hence neither hermetic tightness nor hemostasis of the suture placed on the extreme portions of the stitched-up organ is attained after the magazine and die have been brought apart and the instrument has been withdrawn from the operative wound.

In practical surgery the semiperimeter of a compressed organ may frequently be in excess of the distance between the lateral sides of the frame of an instrument applied, since it is hard to estimate by eye the size and semiperimeter of a hollow organ when compressed, and to compare its size with the distance between the lateral frame sides, especially when manipulating deeply in the wound and observability of the operative field is hampered. In such a situation the aforesaid disadvantage is still more demonstrable, inasmuch as the marginal tissues of the organ operated upon are compressed lengthwise the line of the suture being placed and are free to spread out as soon as the instrument is withdrawn from the operative wound, whereby the length of the non-sutured section is still increased.

Whenever good observation of the operative field is provided and an adequately convenient access to the suture is obtained, imperfections of a mechanical suture are quite evident, and the surgeon is in a position of placing auxiliary manual sutures on the extreme sections of the operative wound to provide hemetic tightness and good hemostasis of the suture. However, the instrument proves to be inapplicable in case of surgery under hard-of-access conditions deeply in a narrow operative field where visual control of the suture is difficult, or when it is practically impossible to place additional sutures on the extreme wound sections due to difficulties in passing a thread-fitted needle and performing manual-suture application manipulations. The instrument is also inapplicable in cases where a short stump of the stitched-up organ slips off after a mechanical suture has been applied and gets obscured by the surrounding tissues and organs, or when any further effects with a needle and thread upon delicate easily vulnerable tissues, e.g., those of infants. Nonsutured extreme sections of the stitched-up organs might develop profuse postoperative bleeding, disturbed aseptics, or some other complications that might happen fatal to a patient.

SUMMARY OF THE INVENTION

It is an object of the present invention to provide a surgical instrument which would be capable of stitching up organs deeply in a narrow operative wound and seated in hard-of-access places.

It is another object of the present invention to provide a possibility of placing a high-quality and stability staple suture.

It is one more object of the present invention to provide for positive application of stitches of a staple suture to the marginal portions of the organs being stitched up.

An object of the invention is also to provide a detachable staple magazine for the surgical instrument of the character set forth hereinabove, which renders use of the instrument reliable and extends its functional capabilities.

Said and other objects are accomplished due to the fact that, according to the invention, a surgical instrument for placing linear staple sutures comprises a body with a closed rectangular frame, each of the two lateral opposite sides of said frame having a slot on the inner surface of said lateral side close to a third frame side adjacent to the lateral ones, the axis of said slot being parallel to the respective frame lateral side, a die having a plurality of recesses and secured on the third frame side in such a manner that the die extreme portions incorporating extreme recesses are accommodated inside the slots in the frame lateral sides, a staple head mounted in the body opposite to the die and traversably with respect thereto, a detachable stable magazine adapted to be fixed in the staple head stationary with respect thereto and provided with a plurality of staple slots, said staple magazine, when in the suturing position, being set with its portions incorporating extreme staple slots, into the slots on the frame lateral sides opposite to the respective extreme die recesses, a staple ejector movably mounted in the staple head and so arranged as to correspond to the magazine staple slots, an actuator of the staple head and an actuator of the staple ejector, both actuators being accommodated in the body.

It is expedient that those portions of the detachable staple magazine which are accommodated inside the slots on the frame lateral sides be of the same width as said slots.

When the detachable magazine has guide projections for its setting in the staple head, it is expedient that said guide projections be provided on a section defined by the distance between the projections on the frame lateral sides, when in the suturing position.

It is also expedient that those portions of the detachable magazine which correspond to the side grooves defined by the guide projections, and the magazine portions installed inside the slots on the frame lateral sides, be of the same width.

The detachable staple magazine may have a stop shaped as a projection for the magazine to preliminarily fix with respect to the staple head and to the slots on the frame lateral sides.

Each of the frame lateral sides has an opening communicating with the slot and located on the section adjacent to the die.

It is likewise expedient that a projection adjacent to the die be provided on part of each frame lateral sides on the inner surface thereof, and that a slot be provided in said projection and be open on the side opposite to the die.

The aforesaid objects are accomplished also due to the fact that a surgical instrument for placing linear staple sutures, according to the invention, comprises a body with a closed rectangular frame, wherein each of its lateral sides has a projection whose axis is parallel to the respective frame lateral side, a die provided with a plurality of recesses and secured on a frame third side between the lateral sides thereof in such a manner that the die extreme portions incorporating extreme recesses, encompass the respective projection on the frame lateral side, a staple head mounted in the frame opposite to the die and traversably with respect thereto, a detachable staple magazine adapted to be set in the staple head stationary with respect thereto and having a plurality of staple slots and a slot in each of its end faces, said slot corresponding to the projection on the frame lateral side, said projections being for said magazine to set, through the slots in its end faces, in the suturing position, the extreme staple slots of said magazine being located on the portions forming the slots in the end faces and have their respective extreme recesses of the die, which are situated on the die portions encompassing the projections on the frame lateral sides, a staple ejector mounted movably in the staple head and so arranged as to correspond to the magazine staple slots, an actuator of the staple head and an actuator of the staple ejector, both actuators being accommodated in the body.

Provision of the frame lateral (with respect to the die) sides having longitudinal slots on their inner surface in the immediate vicinity of the die, and fitting the die portions incorporating extreme recesses and the magazine portions incorporating extreme staple slots, into these longitudinal slots, makes it possible to ensure high rigidity of the construction of the closed frame and comparatively small cross-sectional dimensions of the stitching mechanism construction elements, as well as to assure application of the suture stitches to the marginal portions of the organs pressed in between the magazine and the die and reliably restricted by the frame lateral sides. The length of the organ being stitched up, which is interposed between the frame lateral sides and pressed between the magazine and the die, is shorter than the length of the suture being placed even though the length of the cross-sectional semiperimeter of the organ, when in a free state, exceeds much the distance between the frame laterial sides. This makes the use of the instrument much more reliable, extends its functional capabilities due to good maneuvrability of the instrument in the operative wound and assures hermetic tightness and hemostasis of the mechanical suture applied. It is due to the aforestated construction features that the instrument is applicable for surgery in hard-of-access and confined places, as well as for stitching up organs having delicate and thin-walled tissues, e.g., in surgery of babies or in vascular surgery involving improved quality of sutures applied.

Provision of a through opening in each of the frame lateral sides on its section adjacent to the die makes formation of stitches on the suture extreme sections reliable and stable in the course of prolonged application of the instrument in surgical practice, this being due to the fact that said opening reduces to a great extent a possitility of soiling the die extreme recesses and the portions of the longitudinal slots in the frame lateral sides which are adjacent to the die, improves visual control and simplifies washing and cleaning of this portion of the instrument from blood after surgery. This feature is of great importance, since when polluted the extreme die recesses and the sections of the longitudinal slots adjacent thereto will fail to provide a required quality and stability of the stitch formation process, especially in case of a comparatively small staple size, e.g., with a staple wire diameter less than 0.2 mm, which is the case with stitching up small-size organs, for instance, in surgery of infants.

Thus, the aforestated construction features of the instruments enable its expanded functional capabilities, improve the quality, stability and reliability of mechanical suture application within prolonged service life of the instrument. To sum up, all this makes it possible to reduce the number of postoperative complications and simplify surgeon's work.

BRIEF DESCRIPTION OF THE DRAWINGS

Further objects and advantages of the present invention will become apparent from a consideration of some specific embodiments thereof, reference being made to the accompanying drawings, wherein:

FIG. 1 is a general view of the surgical instrument, according to the invention;

FIG. 2 is a sectional view of the same instrument, taken along the line II—II in FIG. 1;

FIG. 3 is a sectional view of the same instrument, taken along the line III—III in FIG. 2;

FIG. 4 is a sectional view of the same instrument, taken along the line IV—IV in FIG. 3;

FIG. 5 is a sectional view of the same instrument, taken along the line V—V in FIG. 3;

FIG. 6 is a sectional view of the same instrument, taken along the line VI—VI in FIG. 2;

FIG. 13 illustrates another embodiment of the surgical instrument, according to the invention, showing a sectional view of the frame and staple head thereof, taken along the instrument axis;

FIG. 14 is a sectional view of the same instrument, taken along the line XIV—XIV in FIG. 13;

FIG. 15 is a sectional view of the same instrument, taken along the line XV—XV in FIG. 14;

FIG. 19 illustrates one more embodiment of the surgical instrument, according to the invention, showing a sectional view of the frame and staple head thereof, taken along the frame axial plane;

FIG. 20 is a sectional view of the same instrument, taken along the line XX—XX in FIG. 19;

FIG. 21 is a sectional view of the same instrument, taken along the line XXI—XXI in FIG. 19.

DETAILED DESCRIPTION OF THE INVENTION

Figure 7:
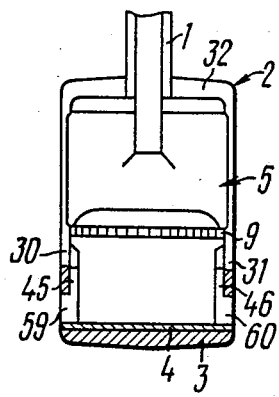
FIG. 7 is a fragmentary, partly sectional view of the same instrument having a solid body frame, according to the invention.

The surgical instrument for placing linear staple sutures of the construction considered herein can find most utility when applied for placing staple sutures in hard-of-access places or deeply in a narrow operative wound. The instrument comprises a body 1 (FIGS. 1, 2) having a closed rectangular frame 2, which carries a die 4 secured on a side 3 of said frame. A staple head 5 is associated with the frame 2 which is situated opposite to the die 4 and mounted traversably towards and away therefrom.

The staple head 5 has a rod 6 (FIGS. 1, 3) accommodated in a slot 7 of the body 1, and a body 8 (FIG. 4). The body 8 accommodates a detachable staple magazine 9 fixed stationary therein and having a housing 9' shaped as a rectangular parallelepiped and a number of staple slots 10 (FIG. 3), a traversable staple ejector 11 arranged so that its prongs 12 correspond to the staple slots 10 of the magazine 9.

The housing 9' of the magazine 9 has two side grooves 13 (FIG. 4) which are adapted to engage, when the magazine 9 is fitted in the staple head 5, with projections 14 provided on the inner surfaces of the body 8 of the staple head 5. To lock the magazine 9 in place in the staple head 5, said magazine has a stop 15 (FIG. 5) shaped as a projection and resting against a face 16 of an opening 17 in the staple head 5.

The staple ejector 11 (FIG. 2) has a rod 18 (FIG. 6) accommodated in the slot 7 (FIG. 2) of the body 1 under the rod 6 of the staple head. An opening 19 (FIG. 3) is provided in the staple head for the staple ejector 11 to pass therein.

The rod 6 (FIG. 2) of the staple head is provided with a hollow tailpiece 20 having an external thread 21 and an internal thread 22. A nut 23 is engaged with the external thread 21, said nut being in fact an actuator of the staple head 5. The nut 23 is locked in the body 1 with the aid of an annular groove 24 adapted to interact with a lug 25 on the body 1.

A screw 26 is engaged with the internal thread 22 of the tailpiece 20, said screw being in fact an actuator of the staple ejector 11. The screw 26 has a cannelure 27 with which the rod 18 of the staple ejector is adapted to interact through a lug 28 (FIG. 6) provided at the end of the rod 18. The screw 26 is provided with a removable handle 29 (FIG. 1).

Sides 30 and 31 of the frame 2, lateral with respect to the die 4, associated the side 3 and an opposite side 32 of the frame 2, thus imparting high rigidity to the latter. The frame 2 may be either solid (FIG. 7) or one of its lateral sides, e.g., the side 30, may be made as a stem 33 (FIG. 1) and mounted detachably. The latter being the case, the frame 2 is made as a U-shaped member 34 (FIGS. 3, 8) and vacant ends 35, 36 of the frame sides 3 and 32 are encompassed by stops 37, 38 (FIG. 9) of the detachable stem 33. For the purpose the stem 33 has an opening 39 into which the vacant end 35 of the frame side 3 is fitted, and is provided with two side slots 40, 41 situated at the placed where the vacant end 36 is engaged with the opposite side 32 of the frame 2, said slots 40, 41 being embraces with a fork 42 at the vacant end 36 of the frame side 32. Retainers 43, 44 are provided at the frame vacant ends 35, 36 (FIGS. 3, 8) for the stem 33 to lock in position. The stem 33 can be detached due to the fact that the U-shaped member of the frame 2 is made springy by virtue of elastic strain of the lateral side 31 rigidly linked with the sides 3 and 32 of the frame 2.

When pressing on the vacant end 35 of the side 3 and on the stem 33 from below upwards against the end 36 of the side 32, the stop 38 (FIGS. 8, 9) of the stem 33 is thrown out of engagement with the retainer 44, thus releasing the stem 33 for its disengagement from the sides 3 and 32. The lateral sides 30, 31 (FIG. 10) of the frame 2 are encompassed by the body 8 of the staple head 5, when in working position, and serve as the guides for the staple head to traverse from the initial to the working position.

It is due to high constructional rigidity of the closed rectangular frame 2 of the body 1 (FIG. 3) that a stable mutual arrangement of the recesses 4' in the die 4 and the staple slots 10 in the magazine 9 is attained when substantial loads are imposed upon the stitching mechanism, resulting from compression of the organs operated upon a single-stage bending deformation of a great number of staples in the course of suturing. Minimized cross-sectional dimensions of the side 3 with the die 4, the lateral sides 30, 31 of the frame 2 and the entire stitching mechanism are attained, accordingly. This in turn provides for good maneuvrability of the instrument in the operative wound and a possibility of placing delicate elastic sutures featuring a small tissue torus.

The lateral sides 30, 31 of the frame 2 have respective longitudinal slots on the inner surface thereof, situated in the immediate vicinity of the die 4. The axis of each of the slots 45, 46 is parallel to the respective lateral side of the frame 2 (FIG. 4). Portions 47, 48 (FIG. 11) of the die 4 incorporating extreme recesses 49, 50 are accommodated inside the longitudinal slots 45, 46. Portions 51, 52 (FIG. 10) of the magazine 9 incorporating extreme staple slots 53, 54 are also accommodated in the longitudinal slots 45, 46 on the lateral sides of the frame 2 (FIGS. 7, 8) when the staple head 5 is in working position corresponding to a required suturing gap.

Figure 12:
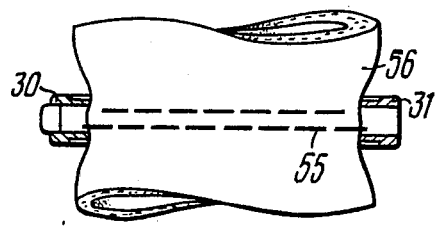
FIG. 12 shows a linear staple suture applied to an organ interposed between the frame lateral sides.

Such a constructional arrangement of the closed rectangular frame 2 of the body 1 and of the staple head 5 with the magazine 9 makes it possible to stitch up organs deeply in a narrow operative wound or in hard-of-access places, assures application of staple sutures 55 (FIG. 12) to the marginal portions of the walls of organs 56 pressed between the magazine and the die even in the cases where the length of the semiperimeter of the cross-sectional dimensions of the organ 56, when in a free state, exceeds the distance between the lateral sides 30, 31 of the frame 2. This renders instrument application under hard-of-access conditions more reliable.

Figure 8:
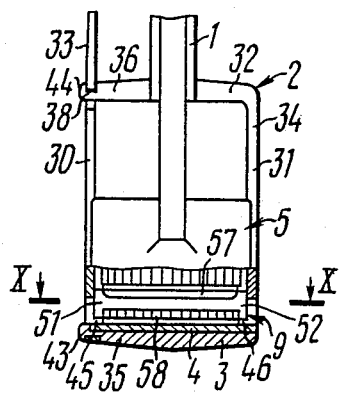
FIG. 8 is a fragmentary, partly sectional view of the same instrument showing its staple head in working position.
Figure 9:
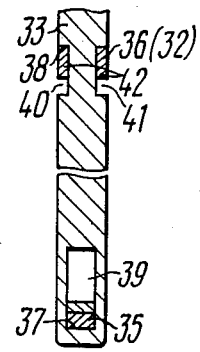
FIG. 9 is a sectional view of the same instrument, taken along the line IX—IX in FIG. 3.
Figure 10:
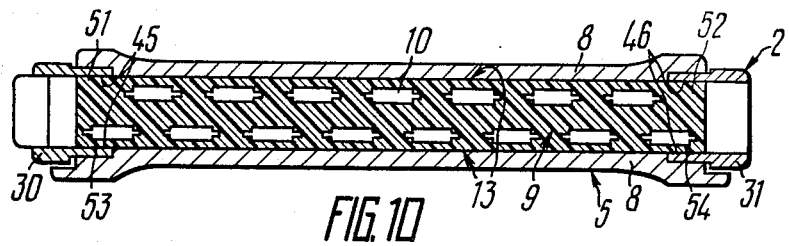
FIG. 10 is a sectional view of the same instrument, taken along the line X—X in FIG. 8.
Figure 11:
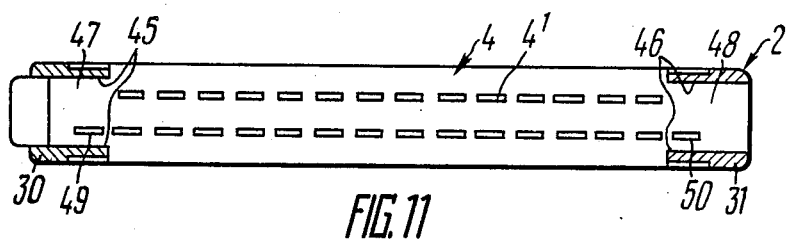
FIG. 11 is a sectional view of the same instrument, taken along the line XI—XI in FIG. 3.

The portions 51, 52 of the detachable magazine 9 (FIG. 10), incorporating the extreme staple slots 53, 54 accommodated inside the slots 45, 46 on the lateral sides 30, 31 of the frame 2, have a width approximately equal to the width of said slots 45, 46, while the portions of the magazine 9 which correspond to the side grooves 13 and to the extreme portions 51, 52 thereof, are equal in width. The lateral walls of the magazine 9 on said sections thereof are coplanar (FIGS. 8, 10).

The side grooves 13 (FIGS. 4, 5) in the magazine 9 are defined by guide projections 57, 58 which are provided on a section confined by the distance from the lateral sides 30, 31 (FIG. 8) of the frame when is the suturing position. The stop 15 (FIG. 5) of the magazine 9 is located on said projection 57 so as to contact the face 16 of the body 8 of the staple head 5 and provide for preliminary fixing of the magazine 9 with respect to the staple head 5 and to the slots 45, 46 (FIG. 3) on the lateral sides of the frame 2. Such a constructional arrangement of the magazine enables convenient replacement of an empty magazine with a staple-loaded one, which may be the case when a number of mechanical staple sutures are to be placed deeply in the operative wound without withdrawal of the frame 2 of the body 1 therefrom, e.g., when two linear sutures have to be placed under hard-of-access conditions and the tissues of the organ being stitched up should be severed between the sutures applied. Such being the case, the application of the first suture is followed by replacement of the empty magazine in the staple head 5 detached from the frame 2 of the body 1 and withdrawn from the operative wound, whereas the frame 2 of the body 1 embraces the organ stitched up with the first suture and remains deeply in the operative wound. Once the staple-loaded magazine 9 has been fitted into the staple head 5, the stop 15 locks reliably the magazine 9 with respect to the staple head 2 and to the slots 45, 46 on the lateral sides of the frame 2 the instant at which the staple head is instroduced into the operative wound and engaged with the frame 2 of the body 1.

The lateral sides 30, 31 (FIG. 3) of the frame 2 have respective openings 59, 60 in its portions adjacent to the die 4, said openings facing the longitudinal slots 45, 46. The openings 59, 60 provides for convenient access to the extreme recesses 49, 50 (FIG. 11) of the die 4 situated in the longitudinal slots 45, 46 on the frame lateral sides, a feature that practically rules out any danger of polluting the extreme portions 47, 48 of the die 4 located in the longitudinal slots 45, 46 on the lateral sides 30, 31 of the frame 2 and the slots 45, 46 themselves and improves the washing and cleaning conditions of the latter. This also facilitates visual control over the condition of the surfaces of said instrument components within the zone most critical to its functioning. Hence trouble-free instrument operation is provided within a prolonged period of its clinical use.

A respective projection 61, 62 adjacent to the die 4 is provided on part of each lateral side 30, 31 (FIG. 1) of the frame 2 on the inner surface thereof, and the respective longitudinal slot 45, 46 (FIG. 3) is made in each of the projections 61, 62. With the staple head 5 (FIG. 3) in the initial position the portions 51, 52 of the magazine 9, incorporating the extreme staple slots 53, 54, are situated outside the longitudinal slots 45, 46. For the extreme portions 51, 52 of the magazine 9 to engage in the longitudinal slots 45, 46 of the projections 61, 62 on the lateral sides 30, 31 of the closed frame 2 when the staple head 5 travels from the initial to the working position, said slots 45, 46 are made open on the side opposite to the die 4.

Lugs 63 are provided on the rod 6 (FIG. 1) of the staple head 5, engageable with slots on the lateral faces of the slot 7 in the body 1 for the rod 6 to join inseparably with the body 1.

Figure 16:
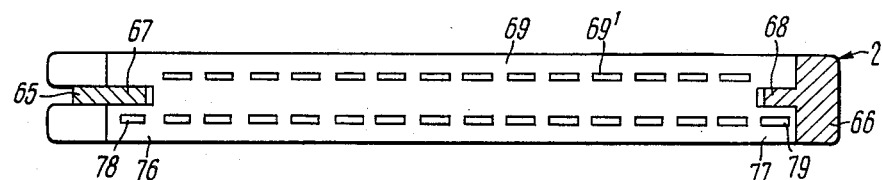
FIG. 16 is a sectional view of the same instrument, taken along the line XVI—XVI in FIG. 14.

In one of the embodiments of the instrument each of lateral sides 65, 66 (FIGS. 13, 14) of the closed rectangular frame 2 has a respective projection 67, 68 is located on part of the respective lateral side 65, 66 adjacent to a die 69. The side 3 mounting the die 69 and the side 32 of the U-shaped member of the frame 2 have at its vacant end a fork 70 (FIG. 15) and a fork 71, respectively. The detachable side of the frame 2 has lateral slots 72, 73 encompassed by the fork 70, and slots 74, 75 encompassed by the fork 71. The die 69 (FIG. 16) is so arranged that its extreme portions 76, 77 incorporating extreme recesses 78, 79 encompass the respective projections on the respective lateral side 65, 66 of the frame 2.

Figure 17:
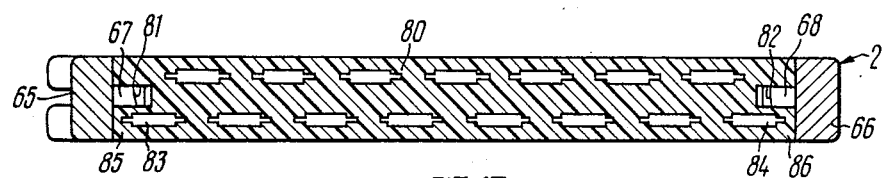
FIG. 17 is a sectional view of the same instrument, taken along the line XVII—XVII in FIG. 14.

A detachable staple magazine 80 (FIG. 17) has a respective slot 81, 82 in each of its end faces, corresponding to the respective projection 67, 68 on the respective lateral side 65, 66 of the frame 2. Extreme staple slots 83, 84 are located on portions 85, 86 of the magazine 80 which establish the end slots 81, 82 and correspond to the extreme recesses 78, 79 (FIG. 16) of the die 69.

Figure 18:
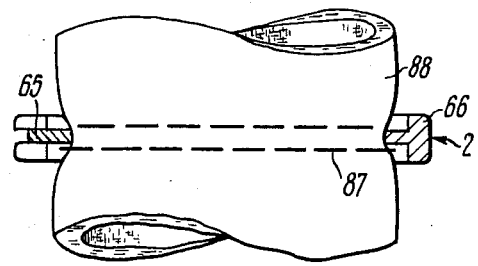
FIG. 18 shows a linear staple suture applied to an organ interposed between the frame lateral sides.

It is due to such a constructional arrangement, likewise the embodiment illustrated in FIGS. 1, 2, 10, 11 that the length of a staple suture 87 (FIG. 18) placed on an organ 88, exceeds the distance between the lateral sides 65, 66 of the frame 2. This ensures application of staple sutures to the marginal sections of the organ tissues pressed between the magazine and the die during the suturing process, enables quality suturing of organs under hard-of-access conditions, and renders instrument application more reliable.

There have been considered hereinbefore the embodiments of the surgical instrument featuring the slot 7 (FIG. 1) of the body 1 opening towards a direction square with the plane of the frame 2. However, the distinguishing features of the instrument of the present invention enable one to obtain the aforediscussed substantial advantages also in the case where a slot 89 (FIG. 19) of the body 1 opens towards a direction coincident with the plane of the frame 2. In such a case the vacant end 36 of the side 32 of the frame 2 has an opening 90 whose faces 91, 92 (FIG. 20) coincide with lateral faces 93, 94 of the slot 89 in the body 1. To provide more rigidity of the mutual arrangement of the faces 91, 92 of the oblong opening 90, the detachable stem 33 (FIG. 21) incorporates restrictors 95, 96 to prevent the thin faces 91, 92 from displacement in a direction square with the plane of the frame 2. The longitudinal slots 45, 46 on the lateral sides 30, 31 of the frame 2, which accommodate the extreme portions of both the die 4 and the magazine 9, are made in the projections 61, 62 of the lateral sides 30, 31 as in the embodiment of the instrument illustrated in FIG. 3.

An instrument having the body 1 with the slot 89 (FIG. 19) opening towards a direction coincident with the plane of the frame 2 may also be made (not shown in the drawing) as illustrated in FIG. 14. In such a case the sides 65, 66 of the frame 2 have the respective projections 67, 68 which are encompassed by the extreme portions 76, 77 (FIG. 16) of the die 69 incorporating the extreme recesses 78, 79 and by the extreme portions 85, 86 (FIG. 17) of the magazine 80 incorporating the extreme staple slots 83, 84, with the magazine 80 in its working position.

Figure 22:
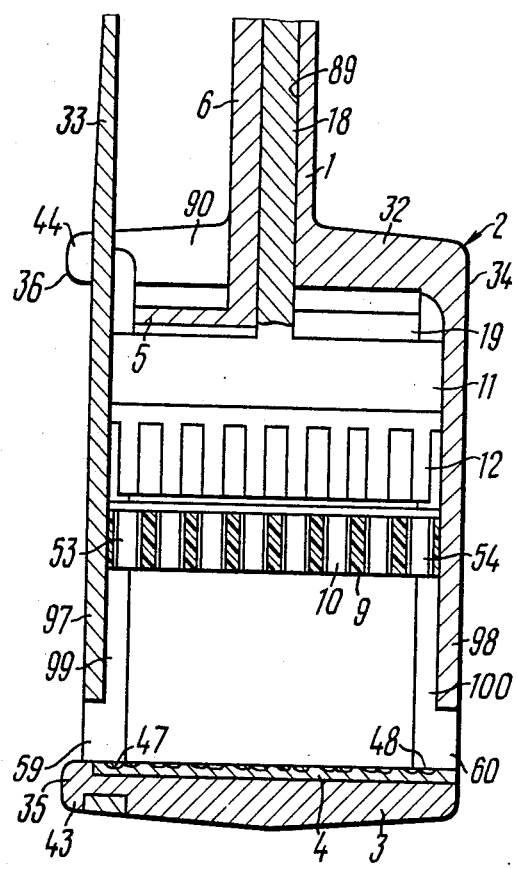
FIG. 22 illustrates still one more embodiment of the surgical instrument, according to the invention, showing a sectional view of the frame and staple head thereof, taken along the frame axial plane.

All the hereinbefore considered embodiments of the instrument illustrated in FIGS. 1 through 21, are far from exhausting completely the potentialities of further embodying the instrument according to the invention. Thus, for instance, FIG. 22 illustrates an embodiment of the instrument, wherein lateral sides 97, 98 of the frame 2 of the body 1 has longitudinal slots 99, 100 running throughout the length of the lateral sides 97, 98. An alternative embodiment of the instrument to the preceding one may be provided (not shown) in the drawing), wherein the projections 67, 68 (FIG. 14) on the lateral sides of the frame 2 of the body 1 encompassed by the extreme portions of the die 69 (FIG. 16) incorporating the extreme recesses 78, 79, and by the extreme portions of the magazine 80 (FIG. 17) incorporating the extreme staple slots, are provided throughout the entire length of the lateral sides of the frame 2.

The detachable staple magazine in all the embodiments of the constructional arrangement of the instrument may be either disposable (made of plastics) or reusable (from metal or other suitable materials).

The instrument of the invention operates as follows.

Before instrument application the staple head 5 and the ejector 11 are set to the initial position FIG. 1, 2), and the detachable stem 33 is disengaged from the U-shaped member of the frame 2. Then the magazine 9 is fitted into the staple head 5, the slots 10 of said magazine having been loaded with staples (omitted in the drawing) beforehand. Once a routine resection preparation procedure of the organ 56 to be sutured, e.g., an intestine seated deeply in the small pelvis has been carried out, the side 3 of the frame 2 is brought under the organ to be sutured, and the organ is encompassed by the die 4 and the magazine 9. Next the detachable stem 33 is fitted onto the vacant ends 35, 36 of the sides 3 and 32 of the U-shaped member 34 of the frame 2, thus closing the latter and confining the organ 56 between the lateral sides 30, 31 of the frame 2. Comparatively small size of the side 3 carrying the die 4, of the lateral sides 30, 31 of the frame 2 and of the cross-section of the entire stitching mechanism enables the instrument to be conveniently brought to the place of suture application. Then the nut 23 is rotated to bring the magazine 9 closer to the die 4 until the amount of the suturing gap (FIG. 9) is obtained, corresponding to the wall thickness of the organ 56 being sutured. The marginal portions of the walls of the organ 56 which are being compressed, are confined within the lateral sides 30, 31 (FIG. 12) of the frame 2 even in cases where the length of the semiperimeter of the organ 56, when in a free state, exceeds the distance between the lateral sides 30, 31 of the frame 2. Thereupon the handle 29 (FIG. 1, 2) of the actuator of the ejector 11 is rotated to drive the staples (omitted in the drawing) out of the magazine 9, which on meeting the die 4, are bent to suture the walls of the organ 56. This done, the resected portion of the stitched-up organ 56 is severed along the lateral surface of the die 4 and magazine 9, the magazine 9 is brought apart from the die 4 by rotating the nut 23, and the instrument is withdrawn from the operative wound, Thanks to the fact that, with the staple head 5 in working position, the extreme recesses 49, 50 (FIG. 11) of the die 4 and the extreme staple slots 53, 54 (FIG. 10) of the magazine 9 are accommodated in the longitudinal slots 45, 46 of the lateral sides 30, 31 of the closed frame 2, the mechanical staple suture 55 (FIG. 12) closes completely the lumen of the stitched-up organ 56.

Whenever the surgical procedure involves application of two linear staple sutures 55 followed by severing the tissue between the sutures applied, which is the case when stitching up, e.g., two intestine ends, application of the first suture is followed by retracting the staple head 5 along with the magazine 9 to the initial position by rotating the nut 23. Then the staple head 5 together with the magazine 9, the ejector 11 and the actuators of the staple head 5 and the ejector 11 is extracted from the frame 2 of the body 1 and withdrawn from the operative wound. The frame 2 of the body 1 is left deeply in the operative wound so that the organ 56 stitched up with the first suture is enclosed by the frame 2. Then the empty magazine is replaced with a loaded one outside the operative wound, whereupon the loaded magazine 9 (FIG. 5) is fitted into the body 8 of the staple head 5 released from the frame 2 and its lateral side 30, until the stop 15 rests against the face 16 of the opening 17 in the staple head 5. Next the staple head 5 is introduced into the operative wound and sunk in the interior space of the frame 2 of the body 1, whereupon the frame 2 is displaced with respect to the first staple suture so that the die 4 secured on the side 3 of the frame 3 should be positioned under the organ 56 being sutured three to five mm away from the line of the previously applied suture. After that the magazine 9 is brought together with the die 4 as close as the amount of the suturing gap, and a second linear staple suture is applied parallel to the first one as it has been described in the preceding case. Then the walls of the organ 56 are severed using a scalpel by moving it along the lateral surface of the magazine 9 and die 4, whereupon the nut 23 is rotated to bring the magazine 9 apart from the die 4, and the instrument is withdrawn from the operative wound.

Fixation of the detachable magazine 9 in the staple head 5 by means of the stop 15 of the magazine 9 makes possible a reliable and fail-safe introduction of the staple head 5 along with the magazine 9 into the interior space of the closed frame 2 when manipulating deeply in the operative wound and under hard-of-access conditions. This construction feature of the instrument enables one to place two parallel sutures under the aforesaid hard-of-access conditions without withdrawing the side 3 of the frame 2 with the die 4 from under the organ 56 stitched up with the first suture for replacing the empty magazine 9 with a staple-loaded one, and without repeated introduction of the side 3 with the die 4 under the stitched-yp organ 56 for placing a second suture. Thereby the risk of inflicting traumatic lesion upon the organ being sutured and the surrounding tissues is reduced, while the range of application techniques of the instrument of the character under consideration is extended, which is of importance for practical surgery.

Whenever use is made of an instrument having the non-separable closed rectangular frame 2 (FIG. 7), the organ being sutured, e.g., the auricular appendage of the heart, is introduced into the space confined between the die 4, the magazine 9 and the lateral sides 30, 31 of the frame 2 in a direction square with the plane of the frame 2. When the excised portion of the organ being sutured is in fact a solid conglomerate which cannot be interposed between the die 4 and the nagazine 9, such being the case with the suturing the the pharynx for laryngocarcinoma, the body 1 should be disengaged from the rest of the instrument before its application. As a result the interior opening of the closed frame 2 of the body 1 is released from the staple head 5 along with the magazine 9 and the staple ejector 11. While passing the conglomerate of the tumor being excised through the wide interior opening of the frame 2, one brings the side 3 of the frame 2 to the place of suture application located between the chin rising thereabove and the thorax, whereupon the staple head 5 in assembly with the rest of the instrument components is engaged with the body 1. All other steps of the instrument application procedure with an instrument having the non-separable closed frame 2 of the body 1 are quite the same as in the case of an instrument comprising the frame 2 with a detachable lateral side. The narrower lateral sides 30, 31 of the frame 2, its side 3 and the magazine 9 provide for convenient setting of the instrument to the suturing position without any danger of inflicting traumatic lesion upon the organs 56 being sutured or the surrounding tissues, as well as application of a delicate suture with a low tissue torus, while the distinguishing features of the stitching mechanism construction preclude any possibility of incompetence or failure of the suture applied to the marginal portions of the stitched-up organ and ensure good hemostatic effect.

There may also be applied, using the aforedescribed, technique, also an instrument having a closed rectangular frame 2 (FIG. 3, 8) but without a removable lateral side 30 in the form of the detachable stem 33. The construction of the instrument enables one to replace the magazines in the staple head 5 with the frame 2 closed and remaining engaged with the staple head 5 and with the all other instrument components. With this purpose in view, one should retract the staple head 5 to the initial position, raise it a little above the frame 2 by pressing the head 5 in a direction square with the plane of the frame, and bring it out of the interior opening of the frame 2 as far as to attain that the lateral side 30 of the frame 2 should not interfere with the removal of the magazine 9 from or its fitting into the staple head 5. The rod 18 (FIG. 2) of the ejector 11 and the rod 6 of the staple head 5 remain accommodated in the slot 7 of the body 1. Once the staple-loaded magazine 9 has been fitted into the body 8 of the staple head 5, one should let the latter down into the interior opening of the frame 2 along with the magazine 9; this done, the instrument is ready for operation.

Operation of the instrument embodiment as shown in FIGS. 13 to 17 differs practically in nothing from its embodiment illustrated in FIGS. 1, 2, 10, 11, the only difference lying in the mutual arrangement of the extreme portions of the magazine incorporating the extreme staple slots, and the die incorporating the extreme recesses and hence in the mutual arrangement of the extreme staples of the mechanical suture being placed (FIGS. 12 and 18) with respect to the frame lateral sides.

Operation of the instrument embodiments as illustrated in FIGS. 19 to 22, featuring the slot 89 (FIG. 19) in the body 1 which opens towards a direction coincident with the plane of the frame, practically does not differ from the originally disclosed embodiment thereof. It must solely be noted that replacement of the magazines in these embodiments of the instrument may be made not until the stem 33 is removed from the U-shaped member 34 of the frame 2.

Thus, the constructional features of the instrument as disclosed in the claims of the invention in contemplation, provide for combination of high rigidity of the instrument stitching mechanism, small cross-sectional dimensions of the frame supporting side and the lateral sides thereof, and of the entire stitching mechanism with a possibility of placing staple sutures whose length exceeds the length of the semiperimeter of organs compressed for suturing. It is due to the aforesaid fact that a surgical suture applied by the instrument is featured by high reliability and stability, as well as by hermetic tightness and good hemostatic properties whenever the length of the semiperimeter of the organ being sutured is shorter than the distance between the frame lateral sides, and that application of a high-quality suture is assured in cases where the length of the semiperimeter of the organ being sutured in the released state is either equal to or exceeds the distance between the frame lateral sides. The marginal portions of the organ being sutured prove to be stitched up at all times, which has been corroborated by experimental studies during which trial suturing procedures have been applied to purposely selected portions of the various organs, such as the lungs, intestines, the cardiac auricular appendage, etc., wherein the length of a whole semiperimeter exceeds the distance between the frame lateral sides. These advantages of the instrument disclosed herein render it applicable in a narrow and deep operative wound; in hard-of-access places, where there is too little space for manipulation with the instrument or with other surgical instrument for placing additional manual sutures after stitching-up the organ with a mechanical suture; whenever application of additional manual sutures is quite undersirable, e.g., in case of suturing fine delicate tissues easily penetrable by needle and thread, or when suturing organs that have previously been exposed to beam therapy; in cases where the stump of the stitched-up organ "escapes" or slips off just after application of a mechanical suture, severing the resected portion of the organ and bringing the magazine and the die apart so that the stump is difficult to identify among the surrounding tissues for revision, or when failure of a mechanical suture might result in profuse bleeding.

Construction of the instrument according to the claims of the present invention improves the quality of applied sutures, extends the functional capabilities of the instruments for suturing organs, and makes their application in the various fields of surgery in infants and adults more reliable.

What is claimed is:

1. A surgical instrument for placing linear staple sutures, comprising:
   a body;
   a closed rectangular frame forming part of said body and established by a first and a second lateral side and a third and a fourth side arranged therebetween;
   a first and a second slot, similar to each other and provided in said respective first and second frame lateral sides, each of said slots having its geometrical axis parallel to said respective first and second lateral sides of said frame;
   a die fixed on said third side of said frame; said die having a plurality of recesses facing an internal side of said frame, and having portions with extreme recesses situated within said first and second slots;
   a staple head mounted in said frame opposite to said die and traversably with respect to said frame;
   a detachable staple magazine adapted to be installed in said staple head; said detachable magazine having a number of staple slots and portions with extreme staple slots and adapted to be set in the suturing position with respect to said frame so that said magazine portions with the extreme staple slots are arranged inside said first and second lateral sides of said frame opposite to said respective portions of said die with said extreme recesses;
   a staple ejector movably fitted in said staple head and so arranged as to correspond to said staple slots of said magazine;
   an actuator of said staple head, accommodated in said body; and
   an actuator of said staple ejector, accommodated in said body.

2. A surgical instrument as claimed in claim 1, wherein said portions of said detachable magazine provided with the extreme staple slots have the same width as said first and second slots in said first and second lateral sides of said frame.

3. A surgical instrument as claimed in claim 2, wherein said detachable magazine has a stop shaped as a projection and adapted to be fixed with respect to said staple head and to said first and second slots in said first and second lateral sides of said frame.

4. A surgical instrument as claimed in claim 1, wherein said detachable magazine has portions confined within said first and second lateral sides in the suturing position, and guides on said confined portions.

5. A surgical instrument as claimed in claim 4, wherein said detachable magazine has a stop shaped as a projection and situated on any of said guides; said stop adapted for said detachable magazine to be fixed with respect to said staple head and to said first and second slots in said first and second lateral sides of said frame.

6. A surgical instrument as claimed in claim 1, wherein said detachable magazine has a stop shaped as a projection and adapted to be fixed with respect to said staple head and to said first and second slots in said first and second lateral sides of said frame.

7. A surgical instrument as claimed in claim 1, wherein a first and a second opening is provided in said first and second lateral side of said frame; said first opening communicating with said second slot.

8. A surgical instrument for placing linear staple sutures, comprising:
   a body;
   a closed rectangular frame forming part of said body and formed by a first and a second lateral side and a third and a fourth side arranged therebetween, a first and a second projection situated respectively on said opposite first and second lateral sides of said frame thereinside and close to said third side adjacent to said first and second lateral sides;
   a first and a second slot, similar to each other and provided in said respective first and second projections, each of said slots having its geometrical axis parallel to said respective first and second lateral sides of said frame; said first and second slots opening on the side facing the fourth side of said frame;
   a die fixed on said third side of said frame; said die having a plurality of recesses facing an internal side of said frame, and having portions with extreme recesses situated within said first and second slots;

a staple head mounted in said frame opposite to said die and traversably with respect to said frame;

a detachable staple magazine adapted to be installed in said staple head; said detachable magazine having a number of staple slots and portions with extreme staple slots and adapted to be set in the suturing position with respect to said frame so that said magazine portions with the extreme staple slots are arranged inside said first and second slots on said first and second lateral sides of said frame opposite to said respective portions of said die with said extreme recesses;

a staple ejector movably mounted in said staple head and so arranged as to correspond to said slots of said magazine;

an actuator of said staple head, accommodated in said body; and an actuator of said staple ejector, accommodated in said body.

9. A surgical instrument as claimed in claim 8, wherein said first and second projections are located on part of said first and second lateral sides.

10. A surgical instrument for placing linear staple sutures, comprising;

a body;

a closed rectangular frame forming part of said body and formed by a first and a second lateral side and a third and a fourth side arranged therebetween;

a first and a second projection situated respectively on said opposite first and second lateral sides of said frame thereinside and close to said third side adjacent to said first and second lateral sides;

a die fixed on said third side of said frame; said die having a plurality of recesses facing an internal side of said frame, and having portions with extreme recesses, said portions encompassing said first and second projections situated on said first and second lateral sides of said frame;

a staple head mounted in said frame opposite to said die and traversably with respect to said frame;

a detachable staple magazine adapted to be installed in said staple head; said detachable magazine having a number of staple slots and a first and second slots in each of the end faces thereof, said slots corresponding to said first and second projections on said first and second lateral sides of said frame, said magazine having portions with extreme staple slots, said magazine portions encompassing said first and second slots in the end faces of said magazine; said detachable magazine adapted to be set in the suturing position with respect to said frame so that said magazine portions with said extreme staple slots are arranged opposite to said respective portions of said die with said extreme recesses;

a staple ejector movably mounted in said staple head and so arranged as to correspond to said staple slots of said magazine;

an actuator of said staple head adapted to be set in said body; and an actuator of said staple ejector adapted to be set in said body.

11. In a surgical instrument for placing linear staple sutures, comprising;

a body;

a closed rectangular frame forming part of said body and formed by a first and a second lateral side and a third and a fourth side arranged therebetween;

a first and a second projection situated respectively on said opposite first and second lateral sides of said frame thereinside and close to said third side adjacent to said first and second lateral sides;

a die fixed on said third side of said frame; said die having a plurality of recesses facing an internal side of said frame, and having portions with extreme recesses, said portions encompassing said first and second projections situated on said first and second lateral sides of said frame;

a staple head mounted in said frame opposite to said die and traversably with respect to said frame;

a detachable staple magazine adapted to be fixed in said staple head and having a body and a number of staple slots in said body;

a staple ejector movably mounted in said staple head and so arranged as to correspond to said staple slots of said magazine;

an actuator of said staple head, accommodated in said body; and an actuator of said staple ejector, accommodated in said body, said body of said detachable staple magazine having a first and a second slot on the end faces thereof, said slots corresponding to said first and second projections on said first and second lateral sides of said frame and said detachable magazine having portions with extreme staple slots, said magazine portions forming said first and second slots in the end faces of said magazine; said detachable staple magazine adapted to be set to the suturing position with respect to said frame so that said magazine portions with the extreme staple slots are arranged opposite to said respective portions of said die with said extreme recesses.

* * * * *